US011633290B2

(12) United States Patent
Valkoun et al.

(10) Patent No.: US 11,633,290 B2
(45) Date of Patent: Apr. 25, 2023

(54) STANDALONE INTERBODY SPACER

(71) Applicant: Astura Medical Inc., Irving, TX (US)

(72) Inventors: Anthony Valkoun, Irving, TX (US); Thomas Purcell, Irving, TX (US)

(73) Assignee: ASTURA MEDICAL INC, Irving, TX (US)

( * ) Notice: Subject to any disclaimer, the term of this patent is extended or adjusted under 35 U.S.C. 154(b) by 0 days.

(21) Appl. No.: 17/491,526

(22) Filed: Sep. 30, 2021

(65) Prior Publication Data

US 2022/0096246 A1 Mar. 31, 2022

Related U.S. Application Data

(60) Provisional application No. 63/085,232, filed on Sep. 30, 2020.

(51) Int. Cl.
*A61F 2/44* (2006.01)
*A61F 2/30* (2006.01)
*A61F 2/46* (2006.01)

(52) U.S. Cl.
CPC ........ *A61F 2/4455* (2013.01); *A61F 2/30749* (2013.01); *A61F 2002/30492* (2013.01); *A61F 2002/4627* (2013.01)

(58) Field of Classification Search
CPC ................ A61F 2/442; A61F 2/445; A61F 2002/30482; A61F 2002/30492; A61F 2002/4627; A61B 17/8042; A61B 17/8047
USPC .............................. 606/289; 623/17.11–17.16
See application file for complete search history.

(56) References Cited

U.S. PATENT DOCUMENTS

| 9,381,093 B1 | 7/2016 | Morris et al. |
| 10,512,547 B2 | 12/2019 | Altarac et al. |
| 2013/0172939 A1* | 7/2013 | Ziolo ................ A61B 17/8605 606/301 |
| 2019/0133778 A1 | 5/2019 | Johnston |

OTHER PUBLICATIONS

International Search Report and Written Opinion in PCT Application No. PCT/US2021/053050 dated Dec. 22, 2021.

* cited by examiner

*Primary Examiner* — Eduardo C Robert
*Assistant Examiner* — Christina NegrelliRodriguez
(74) *Attorney, Agent, or Firm* — Michael R. Shevlin

(57) ABSTRACT

A fastener retention system for a standalone interbody spacer that includes flexible members to configure to rotate from an "unlocked to a "locked" state to cover the screw holes in the interbody space to prevent bone engagement fasteners from backing out.

15 Claims, 5 Drawing Sheets

STANDALONE INTERBODY SPACER

CROSS-REFERENCE TO RELATED APPLICATIONS

This application claims the benefit of U.S. Provisional Application No. 63/085,232 filed Sep. 30, 2020, which is incorporated herein by reference.

FIELD

The present invention relates generally to the field of surgery, and more specifically, to an interbody spacer for placement in intervertebral space between adjacent vertebrae during spinal fixation.

BACKGROUND

A spinal disc can become damaged as a result of degeneration, dysfunction, disease and/or trauma. Conservative treatment can include non-operative treatment through exercise and/or pain relievers to deal with the pain. Operative treatment options include disc removal and replacement using an interbody spacers such as anterior cervical interbody fusion (ACIF), anterior lumbar interbody fusion (ALIF), direct lateral interbody fusion (DLIF) (also known as XLIF), posterior lumbar interbody fusion (PLIF), and transforaminal lumbar interbody fusion (TLIF).

The interbody spacers are placed in the interdiscal space between adjacent vertebrae of the spine, resulting in spinal fusion of the adjacent vertebra wherein two or more vertebrae are joined together (fused) by way of interbody spacers, sometimes with bone grafting, to form a single bone. The current standard of care for interbody fusion requires surgical removal of all or a portion of the intervertebral disc. After removal of the intervertebral disc, the interbody spacer is inserted in the space between the adjacent vertebrae.

The interbody spacer uses bone engagement fasteners to attach the interbody spacer to the adjacent vertebrae to stabilize the intervertebral space and allow fusion of the adjacent vertebrae. During the time it takes for fusion to occur, the bone engagement fasteners may back out of the interbody spacer body and the interbody spacer may inadvertently move.

It would be desirable to provide a fastener retention system to prevent bone engagement fasteners from backing out of the interbody spacer.

SUMMARY

Disclosed is a standalone interbody spacer that includes a fastener retention system to constrain bone engagement fasteners.

The fastener retention system is actuated with a driver device which is provided in the instrumentation system. The fastener retention system consists of one or more flexible members or flexible locking pins, for example, nitinol pins, pressed into bores on the plate component. The flexible members are forced into single shear deflection via a revolving cam barrel which is rigidly affixed to the cam head. The revolving barrel contains radial locking pin pockets that interface with the flexible members and create defined 'clocked' positions for the cam head. The implant plate body contains clearance geometry to allow the flexible members to deflect into while cam is being actuated between radial grooves. The revolving barrel serves as a secondary retention mechanism for the flexible members when in the locked states via the lip created by the clocked grooves.

DETAILED DESCRIPTION

The invention is direct to an interbody spacer that is a modular two-piece design comprising a spacer body and plate with a fastener retention system using one or more flexible members to lock a revolving cam barrel in a locked state for the spine attachment screws. The interbody spacer disclosed may be used for anterior cervical interbody fusion (ACIF), anterior lumbar interbody fusion (ALIF), direct lateral interbody fusion (DLIF) (also known as XLIF), posterior lumbar interbody fusion (PLIF), and transforaminal lumbar interbody fusion (TLIF).

Figure 1:
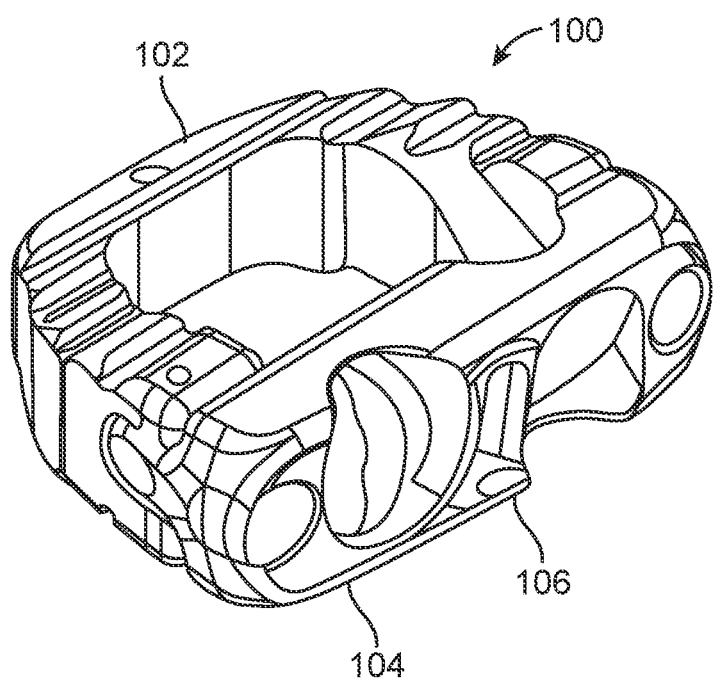
FIG. 1 show a perspective view of an interbody spacer.
Figure 2:
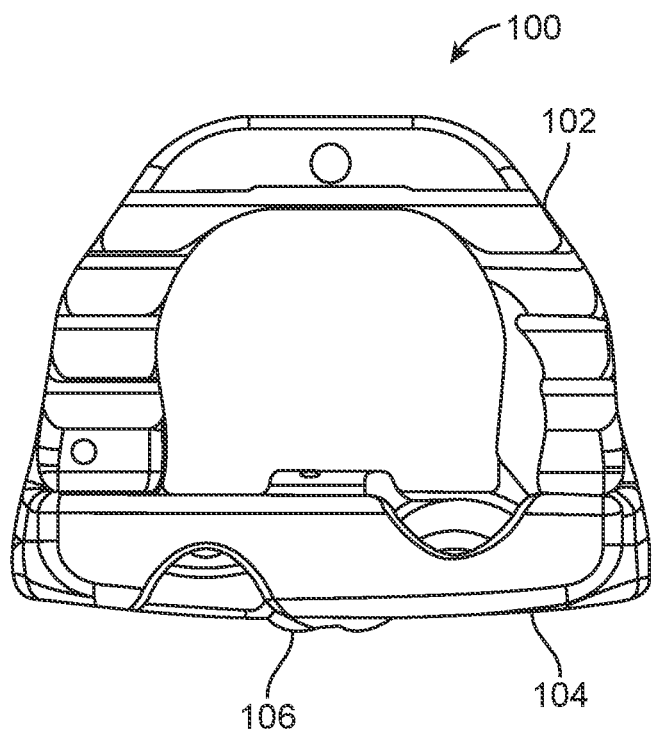
FIG. 2 show a top view of an interbody spacer.

FIGS. 1 and 2 is a perspective view and top view showing one embodiment of an interbody spacer 100 comprising a spacer body 102 coupled a plate 104 and a fastener retention system 106. The spacer body 102 configurations may include various footprints having different widths W, depths D, heights and sagittal profiles.

Figure 3:
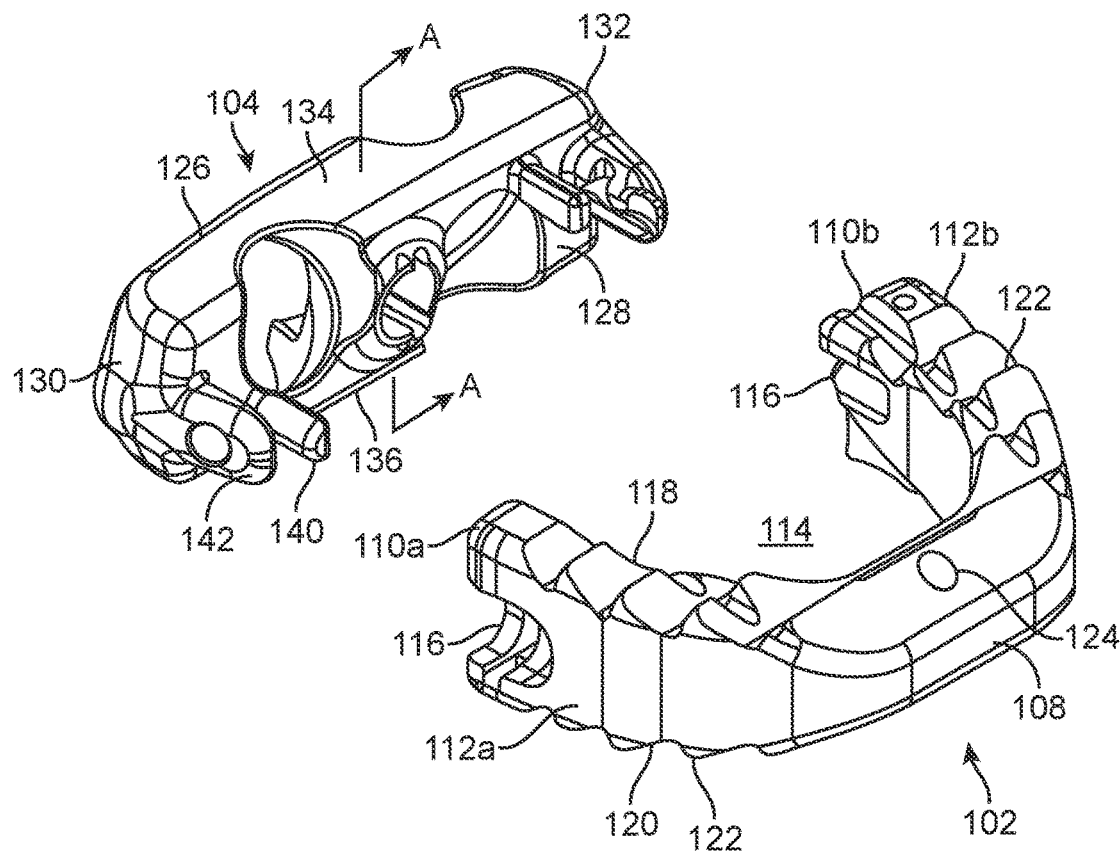
FIG. 3 shows an exploded perspective view showing one embodiment of an interbody spacer

FIG. 3 shows an exploded perspective view showing one embodiment of an interbody spacer 100 comprising a spacer body 102 and a plate 104 and a fastener retention system 106.

The spacer body 102 is u-shape having a closed distal end 108 and open proximal ends 110a, 110b connected by lateral sides 112a, 112b with a central opening 114. The spacer body further includes an upper surface 118 and lower surface 120. The upper and lower surfaces 118, 120 may include teeth 122. The proximal end 110a, 110b of the spacer body 102 includes openings or slots 116. The spacer body 102 may also include a marker pin 124 for locating the spacer 100 on x-ray.

The plate 104 includes a proximal end 126, a distal end 128 and right and left sides 130, 132. The plate further includes an upper surface 134 and lower surface 136. The upper and lower surfaces 134, 136 may include teeth 138. The distal end 128 includes one or more protrusions 140 and engagement arms 142 configured to engage openings or slots 116.

In other embodiments, the interbody spacer 100 may be a one-piece spacer body coupled to the fastener retention system 106.

Figure 4:
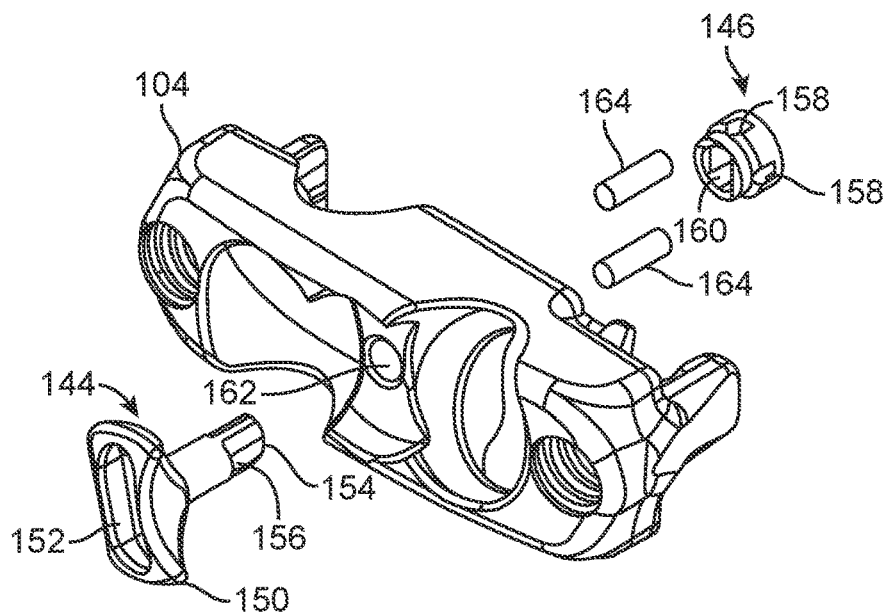
FIG. 4 is a perspective exploded view showing details of the fastener retention system.

FIG. 4 is a perspective exploded view showing details of the fastener retention system 106 having a revolving cam 144 and a revolving barrel 146. The revolving cam 144 includes a cylindrical shaft 148 with a proximal cam head 150 having a tool engagement feature 152, and a distal portion 154 with flat surfaces 156. The revolving barrel 146 includes one or more radial locking pin grooves or locking pin pockets 158 and a central bore 160 having a shape that is configured to receive the distal portion 154 of the revolving cam 144. The plate 104 includes a hole 162 that is sized to slidably receive the cylindrical shaft 148. One or more flexible members or flexible locking pins 164 are configured to couple with the one or more radial grooves locking pin or locking pin pockets 158.

Figure 5:
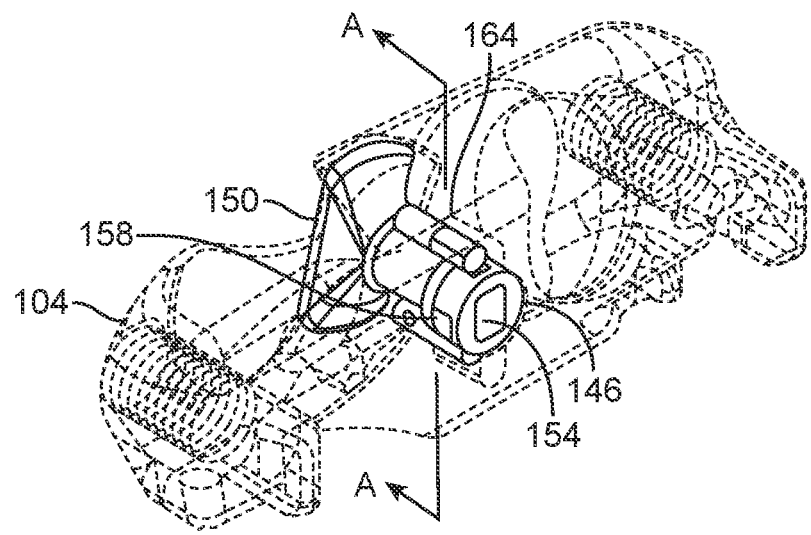
FIG. 5 shows a perspective view showing details of the fastener retention system 106 coupled with the plate.
Figure 6:
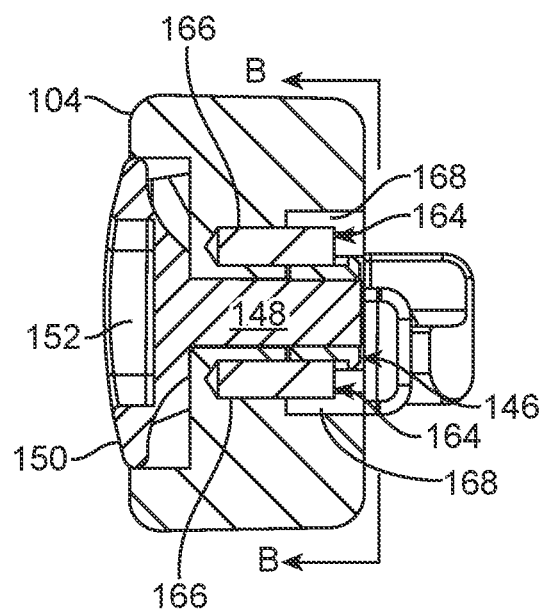
FIG. 6 shows a sectional view A-A of the interbody spacer.
Figure 7:
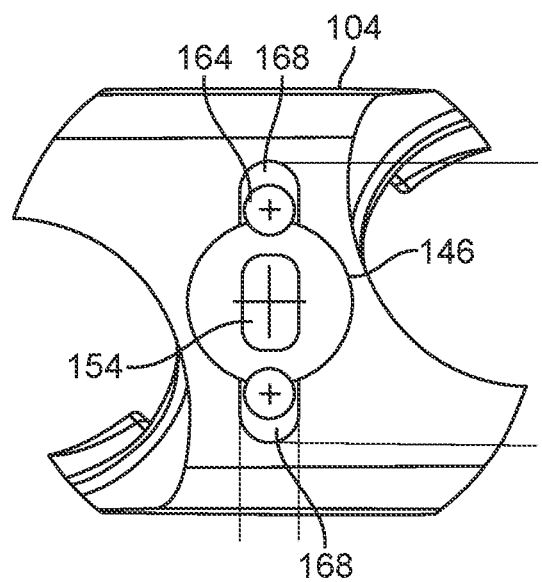
FIG. 7 shows a view B-B of the interbody spacer.

FIGS. 5-7 show a perspective view showing details of the fastener retention system 106 coupled with a plate 104 (in phantom lines), a sectional view at A-A and a view at B-B. While the fastener retention system 106 is shown with plate 104, the fastener retention system 106 may be used with many different types of devices, such as implants, spacers, and bone plates to name a few.

The flexible locking pins 164 are pressed into bores 166 in the plate 104 and couple with the radial locking pin grooves or locking pin pockets 158. While two flexible locking pins 164 are shown in the figures, the fastener retention system 106 will also work with one flexible locking pin 164.

The plate 104 includes clearance geometry 168 that allows the engagement end of the flexible locking pins 164 to deflect into clearance geometry 168 while the revolving barrel 146 is being actuated between radial locking pin grooves or locking pin pockets 158 from an unlocked position to a locked position. The revolving barrel 146 and radial pockets 158 interface with the flexible locking pins 164 and create defined 'clocked' positions for the cam head 150. The revolving barrel 146 serves as a secondary retention mechanism for the pressed flexible locking pins 164 when in the locked states via a lip created by the clocked radial locking pin grooves or locking pin pockets 158.

Figure 8:
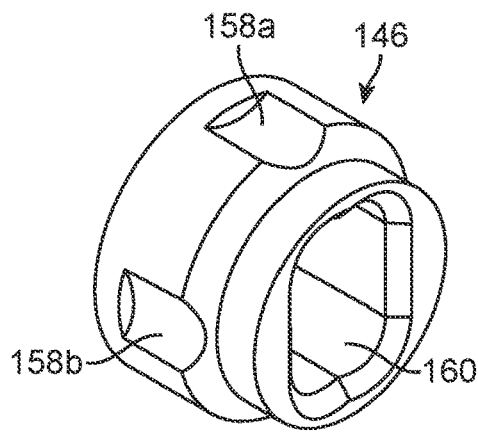
FIG. 8 shows a perspective view of the revolving barrel.

FIG. 8 is a perspective view of the revolving barrel 146 with multiple radial grooves or pockets 158 and the central bore 160 having a shape that is configured to receive the distal portion 154 of the revolving cam 144.

Figure 9:
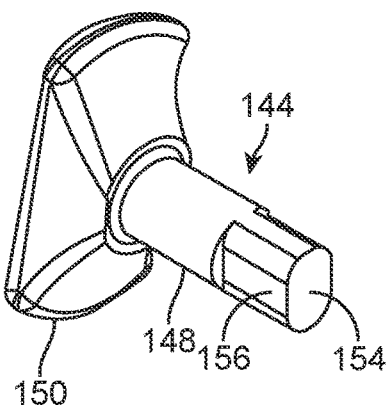
FIG. 9 shows a perspective view of the revolving cam.

FIG. 9 is a perspective view of the revolving cam 144 with the cylindrical shaft 148 and proximal cam head 150 having the tool engagement feature 152 and the distal portion 154 with flat surfaces 156.

Figure 10A:
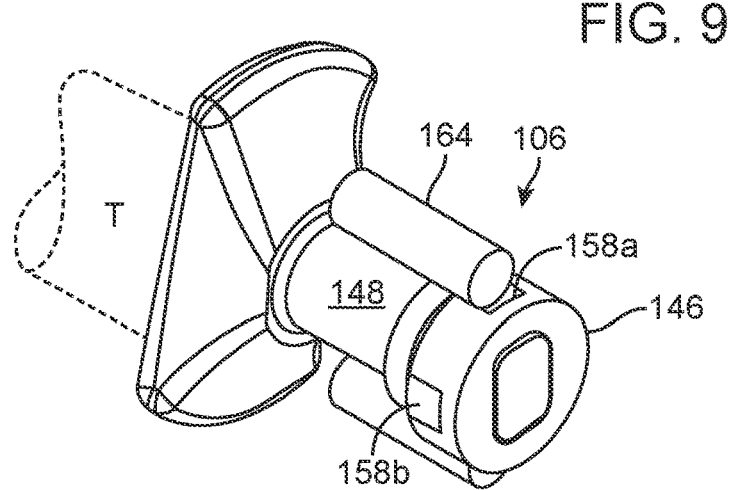
FIGS. 10A and 10B show the fastener retention system in an unlocked position and a locked position.
Figure 10B:
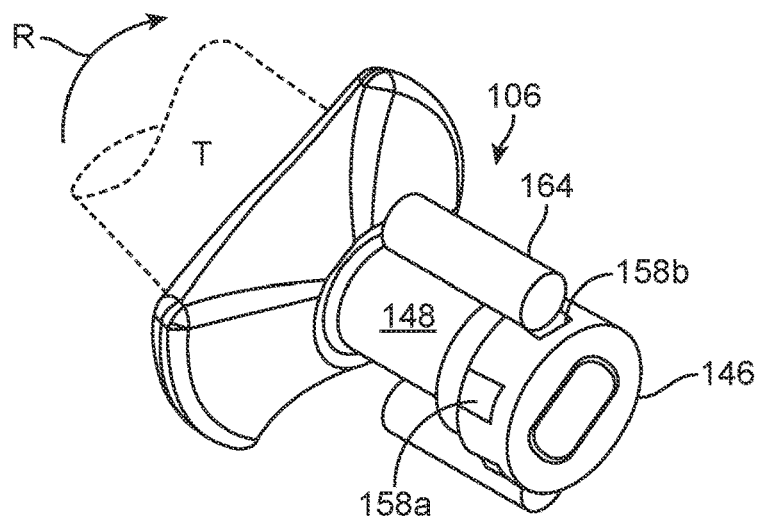

FIG. 10A shows the fastener retention system 106 in the unlocked position and 10B shows the fastener retention system 106 in the locked position. FIG. 10A shows the flexible locking pins 164 in the unlocked position in locking pin pocket 158a of the revolving barrel 146. To lock the fastener retention system 106, an engagement tool T is inserted into the tool engagement feature 152 and rotated R. As the revolving barrel 146 is rotated, the flexible locking pin 164 moves from the locking pin pocket 158a and deforms or flexes into clearance geometry 168 while being actuated between the unlocked radial locking pin pocket 158a to the locked radial locking pin pocket 158b. FIG. 10A shows the flexible locking pins 164 in the locked position in the radial pocket 158b. The radial locking pin pockets 158a, 158b interface with the flexible locking pins 164 create a defined 'clocked' positions for the cam head 150. If the interbody spacer 100 needs to be removed, the fastener retention system 106 may be unlocked by rotating the fastener retention system 106 in the opposite direction.

Figure 11:
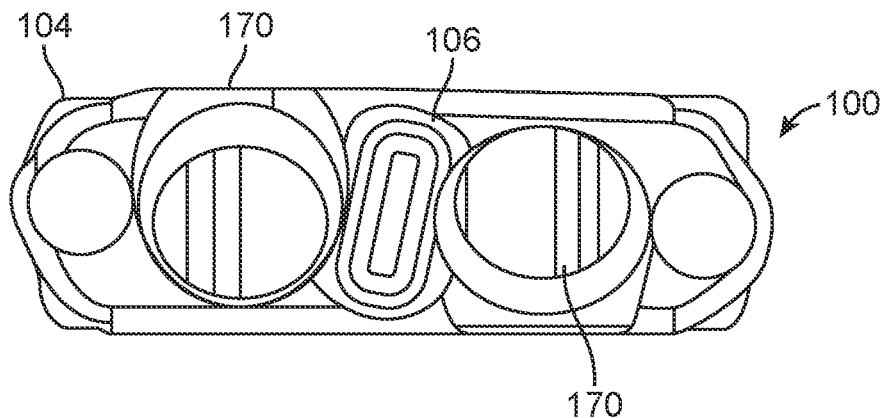
FIG. 11 shows the interbody spacer with the fastener retention system in the unlocked position.

FIG. 11 shows the interbody spacer 100 with the fastener retention system 106 in the unlocked position. The plate 104 includes one or more fastener holes 170 sized to receive bone engagement fasteners 172 configured to anchor the interbody spacer 100 between two vertebrae of the spine. The one or more fastener holes 170 includes one fastener hole tilted at an upward angle so that the engagement fastener engages the vertebra above the interbody spacer 100 and the other fastener hole is tilted at a downward angle so that the bone engagement fastener engages the vertebra below the interbody spacer 100. In the unlocked position the fastener retention system 106 does not interfere with the insertion of the bone engagement fasteners 172 through the fastener holes 170.

Figure 12:
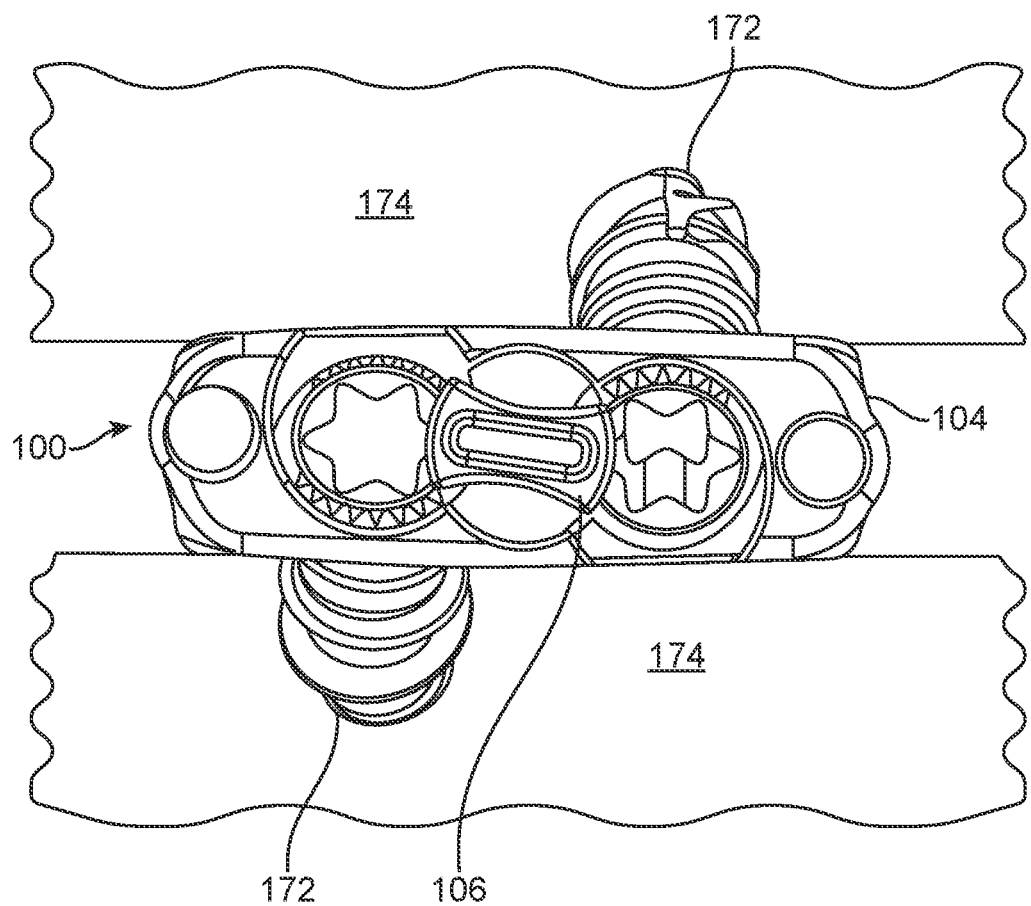
FIG. 12 shows the interbody spacer positioned between two vertebrae of the spine with the fastener retention system in the locked position.

FIG. 12 shows the interbody spacer 100 positioned between two vertebrae 174 of the spine with the fastener retention system 106 in the locked position. The bone engagement fasteners 172 are inserted into the fastener holes 170, with one bone engagement fastener 172 engaging the vertebra 174 above the interbody spacer 100 and the other bone engagement fastener 172 engaging the vertebra 174 below the interbody spacer 100. In the unlocked position the fastener retention system 106 does not interfere with the insertion of the bone engagement fasteners 172 through the fastener holes 170.

Example embodiments of the methods and systems of the present invention have been described herein. As noted elsewhere, these example embodiments have been described for illustrative purposes only and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments but should be defined only in accordance with the following claims and their equivalents.

The invention claimed is:

1. An interbody spacer for placement between adjacent vertebrae comprising:
    a spacer body having one or more fastener holes and one or more flexible locking pins;
    a fastener retention system configured to couple with the spacer body proximate the fastener holes, the fastener retention system having one or more locking pin pockets configured to engage the one or more flexible locking pins, wherein rotation of the fastener retention system is configured to deflect the one or more flexible locking pins from an unlocked locking pin pocket in an unlocked position to a locked locking pin pocket in a locked position;
    wherein when the one or more flexible locking pins are in the unlocked locking pin pocket the fastener retention system does not cover the one or more fastener holes, and when the one or more flexible locking pins are in the locked locking pin pocket, the fastener retention system covers the one or more fastener holes to prevent a bone engagement fastener from backing out.

2. The interbody spacer of claim 1, wherein the spacer includes clearance geometry that allows an engagement end of the flexible locking pins to deflect into the clearance geometry while the fastener retention system is being actuated between locking pin pockets from the unlocked position to the locked position.

3. The interbody spacer of claim 1, wherein a proximal end of the fastener retention system includes a tool engagement feature.

4. The interbody spacer of claim 1, wherein the fastener retention system further includes a revolving cam with a cylindrical shaft coupled to a revolving barrel having the one or more locking pin pockets.

5. The interbody spacer of claim 4, wherein the spacer body includes a hole that is sized to slidably receive the cylindrical shaft.

6. The interbody spacer of claim 1, wherein the flexible locking pins are pressed into bores in a plate and couple with the locking pin pockets.

7. An interbody spacer for placement between adjacent vertebrae comprising:
   a spacer body having one or more fastener holes and one or more flexible locking pins;
   a fastener retention system proximate the one or more fastener holes having one or more locking pin pockets, the fastener retention system being configured to deflect the one or more flexible locking pins from an unlocked locking pin pocket to a locked locking pin pocket, wherein when the one or more flexible locking pins are in the unlocked locking pin pocket the fastener retention system does not cover the one or more fastener holes, and when the one or more flexible locking pins are in the locked locking pin pocket, the fastener retention system covers the one or more fastener holes to prevent a bone engagement fastener from backing out.

8. The interbody spacer of claim 7, wherein the spacer includes clearance geometry that allows an engagement end of the flexible locking pins to deflect into the clearance geometry while the fastener retention system is being actuated between locking pin pockets from an unlocked position to a locked position.

9. The interbody spacer of claim 7, wherein a proximal end of the fastener retention system includes a tool engagement feature.

10. The interbody spacer of claim 7, wherein the fastener retention system further includes a revolving cam with a cylindrical shaft coupled to a revolving barrel having the one or more locking pin pockets.

11. The interbody spacer of claim 10, wherein the spacer body includes a hole that is sized to slidably receive the cylindrical shaft.

12. The interbody spacer of claim 7, wherein the flexible locking pins are pressed into bores in a plate and couple with the locking pin pockets.

13. A fastener retention system comprising:
   a revolving cam having a cylindrical shaft with a proximal cam head and distal revolving barrel, the cylindrical shaft being configured to engage a bore of a medical device proximate one or more fastener holes;
   one or more locking pin pockets in the revolving barrel with the one or more locking pin pockets for a locked position and the one or more locking pin pockets for an unlocked position;
   one or more flexible locking pins configured to engage the one or more locking pin pockets, wherein when the revolving barrel is rotated, the one or more flexible locking pins move from an unlocked locking pin pocket to a locked locking pin pocket;
   wherein when the one or more flexible locking pins are in the unlocked locking pin pocket the fastener retention system does not cover the one or more fastener holes, and when the one or more flexible locking pins are in the locked locking pin pocket, the fastener retention system covers the one or more fastener holes to prevent a bone engagement fastener from backing out.

14. The interbody spacer of claim 13, wherein the spacer body includes a hole that is sized to slidably receive the cylindrical shaft.

15. The interbody spacer of claim 13, wherein the flexible locking pins are pressed into bores in the medical device and couple with the locking pin pockets.

\* \* \* \* \*